United States Patent
El-Sherbeini et al.

(10) Patent No.: US 6,870,041 B1
(45) Date of Patent: Mar. 22, 2005

(54) **MURE PROTEIN AND GENE OF *PSEUDOMONAS AERUGINOSA***

(75) Inventors: Mohamend El-Sherbeini, Westfield, NJ (US); Barbara Azzolina, Denville, NJ (US)

(73) Assignee: Merck & Co., Inc., Rahway, NJ (US)

( * ) Notice: Subject to any disclaimer, the term of this patent is extended or adjusted under 35 U.S.C. 154(b) by 108 days.

(21) Appl. No.: 10/070,775

(22) PCT Filed: Sep. 11, 2000

(86) PCT No.: PCT/US00/24743

§ 371 (c)(1),
(2), (4) Date: Mar. 7, 2002

(87) PCT Pub. No.: WO01/19843

PCT Pub. Date: Mar. 22, 2001

Related U.S. Application Data (60) Provisional application No. 60/154,117, filed on Sep. 15, 1999.

(51) Int. Cl.[7] .......................... C07H 21/04; C12N 15/00; C12N 15/09
(52) U.S. Cl. .................... 536/23.7; 435/69.3; 435/320.1
(58) Field of Search ................................ 536/23.7, 23.2, 536/24.3–24.33; 435/69.3, 71.1, 320.1

(56) References Cited

U.S. PATENT DOCUMENTS

| 6,251,647 | B1 | * | 6/2001 | de Lencastre et al. | ...... 435/193 |
| 6,551,795 | B1 | * | 4/2003 | Rubenfield et al. | ........ 435/69.1 |

OTHER PUBLICATIONS

Liao et al. timicrob. Agents Chemother. 39: 1971–1974, 1995.*

* cited by examiner

*Primary Examiner*—S. Devi
(74) *Attorney, Agent, or Firm*—Michael D. Yablonsky; Jack L. Tribble (57) ABSTRACT

This invention provides isolated polynucleotides that encode the MurE protein of *Pseudomonas aeruginosa*. Purified and isolated MurE recombinant proteins are also provided. Nucleic acid sequences which encode functionally active MurE proteins are described. Assays for the identification of modulators of the of expression of murE and inhibitors of the activity of MurE, are also provided.

4 Claims, 3 Drawing Sheets

FIG. 1A

```
  1   atgcctatgagcctgagccaactgtttccccaggccgagcgcgatctgctgatccgcgag    60
      tacggatactcggactcggttgacaaaggggtccggctcgcgctagacgactaggcgctc
      MetProMetSerLeuSerGlnLeuPheProGlnAlaGluArgAspLeuLeuIleArgGlu 61   ctgaccctggatagccacggcgttcgtccggtcgacctgttcctgacggttccgggcggg   120
      gactgggacctatcggtgccgcaagcaggccagctggacaaggactgccaaggcccgccc
      LeuThrLeuAspSerHisGlyValArgProValAspLeuPheLeuThrValProGlyGly 121   caccaggatggtcgtgcgcacatcgccgatgccctgaccaagggcgcgactgccgtggct   180
      gtggtcctaccagcacgcgtgtagcggctacgggactggttcccgcgctgacggcaccga
      HisGlnAspGlyArgAlaHisIleAlaAspAlaLeuThrLysGlyAlaThrAlaValAla 181   tacgaggcggaaggcgccggagagttgccgcccagcgatgcgccgctgatcgcggtgaag   240
      atgctccgccttccgcggcctctcaacggcgggtcgctacgcggcgactagcgccacttc
      TyrGluAlaGluGlyAlaGlyGluLeuProProSerAspAlaProLeuIleAlaValLys 241   gggctggccgcgcaactgtcggcggtcgccgggcgtttctacggcgagccgagccgcggg   300
      cccgaccggcgcgttgacagccgccagcggcccgcaaagatgccgctcggctcggcgccc
      GlyLeuAlaAlaGlnLeuSerAlaValAlaGlyArgPheTyrGlyGluProSerArgGly 301   ctggacctgatcggcgtcaccggcaccaacggcaagaccagcgtcagccaactggtggcc   360
      gacctggactagccgcagtggccgtggttgccgttctggtcgcagtcggttgaccaccgg
      LeuAspLeuIleGlyValThrGlyThrAsnGlyLysThrSerValSerGlnLeuValAla 361   caggccctggatctgctcggcgagcgctgcggcatcgtcggcaccctcggcaccggtttc   420
      gtccgggacctagacgagccgctcgcgacgccgtagcagccgtgggagccgtggccaaag
      GlnAlaLeuAspLeuLeuGlyGluArgCysGlyIleValGlyThrLeuGlyThrGlyPhe 421   tacggcgccctggagagcggccggcacaccacgccggacccgctcgcggtgcaggccacg   480
      atgccgcgggacctctcgccggccgtgtggtgcggcctgggcgagcgccacgtccggtgc
      TyrGlyAlaLeuGluSerGlyArgHisThrThrProAspProLeuAlaValGlnAlaThr 481   ctggccacgctgaagcaggccggcgcccgcgcggtagcgatggaagtgtcttcccacggc   540
      gaccggtgcgacttcgtccggccgcgggcgcgccatcgctaccttcacagaagggtgccg
      LeuAlaThrLeuLysGlnAlaGlyAlaArgAlaValAlaMetGluValSerSerHisGly 541   ctcgaccagggccgcgtggcggcgctcggcttcgatatcgcggtgttcaccaatctgtcc   600
      gagctggtcccggcgcaccgccgcgagccgaagctatagcgccacaagtggttagacagg
      LeuAspGlnGlyArgValAlaAlaLeuGlyPheAspIleAlaValPheThrAsnLeuSer 601   cgcgaccacctcgactatcacggttcgatggaagcctatgccgccgccaaggccaagctg   660
      gcgctggtggagctgatagtgccaagctaccttcggatacggcggcggttccggttcgac
      ArgAspHisLeuAspTyrHisGlySerMetGluAlaTyrAlaAlaAlaLysAlaLysLeu 661   ttcgcctggccggacctgcgctgccgggtgatcaacctggacgacgatttcggccgtcga   720
      aagcggaccggcctggacgcgacggcccactagttggacctgctgctaaagccggcagct
      PheAlaTrpProAspLeuArgCysArgValIleAsnLeuAspAspAspPheGlyArgArg 721   ctggccggcgaggagcaggactcggagctgatcacctacagcctcaccgacagctcggcg   780
      gaccggccgctcctcgtcctgagcctcgactagtggatgtcggagtggctgtcgagccgc
      LeuAlaGlyGluGluGlnAspSerGluLeuIleThrTyrSerLeuThrAspSerSerAla
```

FIG. 1B

```
 781   ttcctctattgccgcgaagcgcgcttcggcgacgccggcatcgaggcggcgctggtcact    840
       aaggagataacggcgcttcgcgcgaagccgctgcggccgtagctccgccgcgaccagtga
       PheLeuTyrCysArgGluAlaArgPheGlyAspAlaGlyIleGluAlaAlaLeuValThr 841   ccgcacggcgagggcctgctgcgcagcccgttgctcggccgcttcaacctgagcaacctg    900
       ggcgtgccgctcccggacgacgcgtcgggcaacgagccggcgaagttggactcgttggac
       ProHisGlyGluGlyLeuLeuArgSerProLeuLeuGlyArgPheAsnLeuSerAsnLeu 901   ctggcggcggtcggtgcgttgcttggcctgggttatcccctgggcgatatcctccgcact    960
       gaccgccgccagccacgcaacgaaccggacccaataggggacccgctataggaggcgtga
       LeuAlaAlaValGlyAlaLeuLeuGlyLeuGlyTyrProLeuGlyAspIleLeuArgThr 961   ttgccgcaactgcaggggccggtcggccgcatgcagcgcctgggaggcggcggcaagccg   1020
       aacggcgttgacgtccccggccagccggcgtacgtcgcggaccctccgccgccgttcggc
       LeuProGlnLeuGlnGlyProValGlyArgMetGlnArgLeuGlyGlyGlyLysPro 1021   ctggtggtggtggactacgcgcatactcccgacgccctggaaaaagtcctggaggccctg   1080
       gaccaccaccacctgatgcgcgtatgagggctgcgggaccttttcaggacctccgggac
       LeuValValValAspTyrAlaHisThrProAspAlaLeuGluLysValLeuGluAlaLeu 1081   cgtccgcacgcggccgcgcgcctgctgtgcctgttcggctgcggtggcgatcgcgatgcc   1140
       gcaggcgtgcgccggcgcgcggacgacacggacaagccgacgccaccgctagcgctacgg
       ArgProHisAlaAlaAlaArgLeuLeuCysLeuPheGlyCysGlyGlyAspArgAspAla 1141   ggcaagcgtccgctgatggctgcgatcgccgaacgcctggcggatgaggtgctggtcacc   1200
       ccgttcgcaggcgactaccgacgctagcggcttgcggaccgcctactccacgaccagtgg
       GlyLysArgProLeuMetAlaAlaIleAlaGluArgLeuAlaAspGluValLeuValThr 1201   gacgacaacccgcgcaccgaggccagtgcggcgatcatcgccgatatccgcaaaggcttc   1260
       ctgctgttgggcgcgtggctccggtcacgccgctagtagcggctataggcgtttccgaag
       AspAspAsnProArgThrGluAlaSerAlaAlaIleIleAlaAspIleArgLysGlyPhe

1261   gctgccgctgacaaggttaccttcctgccgtcgcgcggtgaggcgatcgcccatctgatc   1320
       cgacggcgactgttccaatggaaggacggcagcgcgccactccgctagcgggtagactag
       AlaAlaAlaAspLysValThrPheLeuProSerArgGlyGluAlaIleAlaHisLeuIle 1321   gcttccgctgcggtggatgacgtggtgctcctggccggcaagggtcacgaggattatcag   1380
       cgaaggcgacgccacctactgcaccacgaggaccggccgttcccagtgctcctaatagtc
       AlaSerAlaAlaValAspAspValValLeuLeuAlaGlyLysGlyHisGluAspTyrGln 1381   gagatcgacggcgtacgccatccgttctccgacatcgagcaggccgagcgcgccctggcc   1440
       ctctagctgccgcatgcggtaggcaagaggctgtagctcgtccggctcgcgcgggaccgg
       GluIleAspGlyValArgHisProPheSerAspIleGluGlnAlaGluArgAlaLeuAla 1441   gcctgggaggtgccgcatgcttgagcctcttcgcctcagccagttgacggtcgcgctgg   1500
       cggaccctccacggcgtacgaactcggagaagcggagtcggtcaactgccagcgcgacc
       AlaTrpGluValProHisAla
```

MURE PROTEIN AND GENE OF PSEUDOMONAS AERUGINOSA

CROSS-REFERENCE TO RELATED APPLICATIONS

This application claims the benefits of U.S. Provisional Application Ser. No. 60/154,117, filed on Sep. 15, 1999 and is a National Stage Filing of PCT/US00/24743, having an International Filing Date of Sep. 11, 2000.

STATEMENT REGARDING FEDERALLY-SPONSORED R&D

Not applicable.

REFERENCE TO MICROFICHE APPENDIX

Not applicable.

FIELD OF THE INVENTION

This invention relates to the genes and enzymes involved in cell wall synthesis in bacteria, and particularly to the inhibition of such enzymes.

BACKGROUND OF THE INVENTION

The bacterial cell wall plays a pivotal role in maintaining the cell shape and integrity. It is also a dynamic structure that permits cell expansion and division. Compounds that interfere with the biosynthesis or integrity of this compartment are bactericidal. The bacterial cell wall is comprised of peptidoglycan (PG), a network of polysaccharide chains cross-linked by short peptides (Rogers, H. J., H. R. Perkins, and J. B. Ward, 1980, Biosynthesis of peptidoglycan. p. 239–297. In Microbial cell walls and membranes. Chapman & Hall Ltd. London). Biosynthesis of PG can be divided into three functional stages. Stage I reactions takes place in the cytoplasm and includes the activities of MurA-through MurF leading to the synthesis of PG nucleotide precursors. Stage II include membrane reactions catalyzed by Mra Y and MurG. Stage III are mediated by Penicillin-binding proteins in the periplasmic space (Bugg, T. D. H. and Walsh, C. T. 1992. Intracellular steps of bacterial cell wall peptidoglycan biosynthesis: enzymology, antibiotics, and antibiotic resistance. Nat. Prod. Rep. 9, 199–215).

A basic repeating structure of PG consists of the disaccharides N-acetylglucosamine (GlucNAc) and N-acetylmuramic acid (MurNAc). The GlucNAc and the MurNAc disaccharides are cross-linked by b-1,4-glycosidic linkages. The MurNAc is linked to a side chain of tetra- or pentapeptide consisting of L-alanine, D-glutamate, m-diaminopimelic acid and ending in either D-alanine or D-alanyl-D-alanine. Only the tetrapeptide side chain, but not the pentapeptide chain participates in cross-linking.

The successive addition of the amino acids in the above peptide chains is catalyzed by four different ligases during the cytoplasmic steps in the bisynthesis of PG. The genes encoding these enzymes are essential for growth validating each of them as antibiotic target. Several lines of evidence support the notion that these ligases are potential target for new antibiotics. These enzymes are highly specific and present in both Gram(−) and Gram (+) bacteria (Bugg, T. D. H. and Walsh, C. T. 1992.).

MurE, the meso-diaminopimelic acid-adding enzyme is an ATP-dependent amino acid ligase that is responsible for the formation of UDP-MurNAc-L-ala-D-Glu-m-Dap (Michaud C, D. Mengin-Lecreulx, J. van Heijenoort, D. Blanot. 1990. Over-production, purification and properties of the uridine-diphosphate-N-acetylmuramoyl-L-alanyl-D-glutarnate:meso-2,6-diaminopimelate ligase from Escherichia coli. Eur J Biochem 194(3):853–861). Inhibitors of this enzyme could lead to new antibiotics for treating infections with Gram (-ve) bacteria such as Pseudomonas aeruginosa.

SUMMARY OF THE INVENTION

Polynucleotides and polypeptides of Pseudomonas aeruginosa MurE, an enzyme involved in bacterial cell wall biosynthesis are provided. The recombinant MurE enzyme is catalytically active in ATP-dependent meso-Diaminopimelic acid (m-Dap) addition reactions. The enzyme is used in in vitro assays to screen for antibacterial compounds that target cell wall biosynthesis. The invention includes the polynucleotides, proteins encoded by the polynucleotides, and host cells expressing the recombinant enzyme, probes and primers, and the use of these molecules in assays.

An aspect of this invention is a polynucleotide having a sequence encoding a Pseudomonas aeruginosa MurE protein, or a complementary sequence. In a particular embodiment the encoded protein has a sequence corresponding to SEQ ID NO:2. In other embodiments, the encoded protein can be a naturally occurring mutant or polymorphic form of the protein. In preferred embodiments the polynucleotide can be DNA, RNA or a mixture of both, and can be single or double stranded. In particular embodiments, the polynucelotide is comprised of natural, non-natural or modified nucleotides. In some embodiments, the internucleotide linkages are linkages that occur in nature. In other embodiments, the internucleotide linkages can be non-natural linkages or a mixture of natural and non-natural linkages. In a most preferred embodiment, the polynucleotide has a sequence shown in SEQ ID NO: 1.

An aspect of this invention is a polynucleotide having a sequence of at least about 25 contiguous nucleotides that is specific for a naturally occurring polynucleotide encoding a Pseudomonas aeruginosa MurE protein. In particular preferred embodiments, the polynucleotides of this aspect are useful as probes for the specific detection of the presence of a polynucleotide encoding a Pseudomonas aeruginosa MurE protein. In other particular embodiments, the polynucleotides of this aspect are useful as primers for use in nucleic acid amplification based assays for the specific detection of the presence of a polynucleotide encoding a Pseudomonas aeruginosa MurE protein. In preferred embodiments, the polynucleotides of this aspect can have additional components including, but not limited to, compounds, isotopes, proteins or sequences for the detection of the probe or primer.

An aspect of this invention is an expression vector including a polynucleotide encoding a Pseudomonas aeruginosa MurE protein, or a complementary sequence, and regulatory regions. In a particular embodiment the encoded protein has a sequence corresponding to SEQ ID NO:2. In particular embodiments, the vector can have any of a variety of regulatory regions known and used in the art as appropriate for the types of host cells the vector can be used in. In a most preferred embodiment, the vector has regulatory regions appropriate for the expression of the encoded protein in gram-negative prokaryotic host cells. In other embodiments, the vector has regulatory regions appropriate for expression of the encoded protein in gram-positive host cells, yeasts, cyanobacteria or actinomycetes. In some preferred embodiments the regulatory regions provide for inducible expression while in other preferred embodiments the regulatory regions provide for constitutive expression. Finally, according to this aspect, the expression vector can be derived from a plasmid, phage, virus or a combination thereof.

An aspect of this invention is host cell comprising an expression vector including a polynucleotide encoding a *Pseudomonas aeruginosa* MurE protein, or a complementary sequence, and regulatory regions. In a particular embodiment the encoded protein has a sequence corresponding to SEQ ID NO:2. In preferred embodiments, the host cell is a yeast, gram-positive bacterium, cyanobacterium or actinomycete. In a most preferred embodiment, the host cell is a gram-negative bacterium.

An aspect of this invention is a process for expressing a MurE protein of *P. aeruginosa* in a host cell. In this aspect a host cell is transformed or transfected with an expression vector including a polynucleotide encoding a *Pseudomonas aeruginosa* MurE protein, or a complementary sequence. According to this aspect, the host cell is cultured under conditions conducive to the expression of the encoded MurE protein. In particular embodiments the expression is inducible or constitutive. In a particular embodiment the encoded protein has a sequence corresponding to SEQ ID NO:2.

An aspect of this invention is a purified polypeptide having an amino acid sequence of SEQ ID NO:2 or the sequence of a naturally occurring mutant or polymorphic form of the protein.

An aspect of this invention is a method of determining whether a candidate compound can inhibit the activity of a *P. aeruginosa* MurE polypeptide. According to this aspect a polynucleotide encoding the polypeptide is used to construct an expression vector appropriate for a particular host cell. The host cell is transformed or transfected with the expression vector and cultured under conditions conducive to the expression of the MurE polypeptide. The cell or a preparation derived therefrom containing the MurE polypeptide is contacted with the candidate. Finally, one measures the activity of the MurE polypeptide in the presence of the candidate. If the activity is lower relative to the activity of the protein in the absence of the candidate, then the candidate is a inhibitor of the MurE polypeptide. In preferred embodiments, the polynucleotide encodes a protein having an amino acid sequence of SEQ ID NO:2 or a naturally occurring mutant of polymorphic form thereof. In other preferred embodiments, the polynucleotide has the sequence of SEQ ID NO: 1. In particular embodiments, the relative activity of MurE is determined by comparing the activity of the MurE in a host cell or a preparation derived therefrom containing the MurE polypeptide. In some embodiments, the host cell is disrupted and the candidate is contacted to the released cytosol. In other embodiments, the cells can be disrupted after contacting with the candidate and before determining the activity of the MurE protein. Finally, according to this aspect the relative activity can determined by comparison to a previously measured or expected activity value for the MurE activity in the host, or preparation, under the conditions. However, in preferred embodiments, the relative activity is determined by measuring the activity of the MurE in a control cell, or preparation, that was not contacted with a candidate compound. In particular embodiments, the host cell is a pseudomonad and the protein inhibited is the MurE produced by the pseudomonad.

An aspect of this invention is a compound that is an inhibitor of a *P. aeruginosa* MurE protein an assay described herein. In preferred embodiments, the compound is an inhibitor of a *P. aeruginosa* MurE protein produced by a host cell comprising an expression vector of this invention. In most preferred embodiments, the compound is also an inhibitor of MurE protein produced by a pathogenic strain *P. aeruginosa* and also inhibits the growth of said pseudomonad.

An aspect of this invention is a pharmaceutical preparation that includes an inhibitor of *P. aeruginosa* MurE and a pharmaceutically acceptable carrier.

An aspect of this invention is a method of treatment comprising administering a inhibitor of the *P. aeruginosa* MurE to a patient. The treatment can be prophylactic or therapeutic. In preferred embodiments, the appropriate dosage for a particular patient is determined by a physician.

By "about" it is meant within 10–20% greater or lesser than particularly stated.

As used herein an "inhibitor" is a compound that interacts with and inhibits or prevents a polypeptide of MurE from catalyzing the ATP-dependent addition of m-Dap to the D-glutamate residue of the UDP-N-acetylmuramyl-L-alanine-D-Glutamine precursor.

As used herein a "modulator" is a compound that interacts with an aspect of cellular biochemistry to effect an increase or decrease in the amount of a polypeptide of MurE present in, at the surface or in the periplasm of a cell, or in the surrounding serum or media. The change in amount of the MurE polypeptide can be mediated by the effect of a modulator on the expression of the protein, e.g., the transcription, translation, post-translational processing, translocation or folding of the protein, or by affecting a component(s) of cellular biochemistry that directly or indirectly participates in the expression of the protein. Alternatively, a modulator can act by accelerating or decelerating the turnover of the protein either by direct interaction with the protein or by interacting with another component(s) of cellular biochemistry which directly or indirectly effects the change.

All of the references cited herein are incorporated by reference in their entirety as background material.

BRIEF DESCRIPTION OF THE DRAWINGS

FIGS. 1A & 1B. Nucleotide sequence (SEQ ID NO: 1) and the predicted amino acid sequence (SEQ ID NO:2) of *P. aeruginosa* murE. The amino acid sequence (SEQ ID NO:2) is presented in three-letter code.

DETAILED DESCRIPTION OF THE INVENTION

This invention provides polynucleotides and polypeptides of a cell wall biosynthesis gene from *Pseudomonas aeruginosa*, referred to herein as MurE. The polynucleotides and polypeptides are used to further provide expression vectors, host cells comprising the vectors, probes and primers, antibodies against the MurE protein and polypeptides thereof, assays for the presence or expression of MurE and assays for the identification of modulators and inhibitors of MurE.

Bacterial MurE, UDP-N-acetylmuramoyl-L-alanyl-D-glutamate:meso-2,6-diaminopimelate ligase, a cytoplasmic peptidoglycan biosynthetic enzyme, catalyzes the ATP-dependent addition of m-Dap to the D-Glutamine residue of the UDP-N-acetylmuramyl-L-alanine-D-Glutamine precursor.

The murE gene was cloned from *Pseudomonas aeruginosa*. Sequence analysis of the *P. aeruginosa* murE gene revealed an open reading frame of 487 amino acids. The deduced amino acid sequence of *P. aeruginosa* MurE is homologous to MurE from *Escherichia coli* and other bacteria. Recombinant MurE protein from *P. aeruginosa* was over-produced as His-tagged fusion protein in *Escherichia coli* host cells and the enzyme was purified to apparent homogeneity. The recombinant enzyme catalyzed the ATP-dependent addition of diaminopimelic acid to a precursor sugar peptide.

Polynucleotides

Nucleic acids encoding murE from *Pseudomonas aeruginosa* are useful in the expression and production of the *P. aeruginosa* MurE protein. The nucleic acids are also useful in providing probes for detecting the presence of *P. aeruginosa* mur E.

A preferred aspect of the present invention is an isolated nucleic acid encoding a MurE protein of *Pseudomonas aeruginosa*. A preferred embodiment is a nucleic acid having the sequence disclosed in FIG. 1, SEQ ID NO: 1 and disclosed as follows:

```
ATGCCTATGA GCCTGAGCCA ACTGTTTCCC CAGGCCGAGC GCGATCTGCT    (SEQ ID NO: 1)
GATCCGCGAG CTGACCCTGG ATAGCCACGG CGTTCGTCCG GTCGACCTGT
TCCTGACGGT TCCGGGCGGG CACCAGGATG GTCGTGCGCA CATCGCCGAT
GCCCTGACCA AGGGCGCGAC TGCCGTGGCT TACGAGGCGG AAGGCGCCGG
AGAGTTGCCG CCCAGCGATG CGCCGCTGAT CGCGGTGAAG GGGCTGGCCG
CGCAACTGTC GGCGGTCGCC GGGCGTTTCT ACGGCGAGCC GAGCCGCGGG
CTGGACCTGA TCGGCGTCAC CGGCACCAAC GGCAAGACCA GCGTCAGCCA
ACTGGTGGCC CAGGCCCTGG ATCTGCTCGG CGAGCGCTGC GGCATCGTCG
GCACCCTCGG CACCGGTTTC TACGGCGCCC TGGAGAGCGG CCGGCACACC
ACGCCGGACC CGCTCGCGGT GCAGGCCACG CTGGCCACGG TGAAGCAGGC
CGGCGCCCGC GCGGTAGCGA TGGAAGTGTC TTCCCACGGC CTCGACCAGG
GCCGCGTGGC GGCGCTCGGC TTCGATATCG CGGTGTTCAC CAATCTGTCC
CGCGACCACC TCGACTATCA CGGTTCGATG GAAGCCTATG CCGCCGCCAA
GGCCAAGCTG TTCGCCTGGC CGGACCTGCG CTGCCGGGTG ATCAACCTGG
ACGACGATTT CGGCCGTCGA CTGGCCGGCG AGGAGCAGGA CTCGGAGCTG
ATCACCTACA GCCTCACCGA CAGCTCGGCG TTCCTCTATT GCCGCGAAGC
GCGCTTCGGC GACGCCGGCA TCGAGCCGGC GCTGGTCACT CCGCACGGCG
AGGGCCTGCT GCGCAGCCCG TTGCTCGGCC GCTTCAACCT GAGCAACCTG
CTGGCGGCGG TCGGTGCGTT GCTTGGCCTG GGTTATCCCC TGGGCGATAT
CCTCCGCACT TTGCCGCAAC TGCAGGGGCC GGTCGGCCGC ATGCAGCGCC
TGGGAGGCGG CGGCAAGCCG CTGGTGGTGG TGGACTACGC GCATACTCCC
GACGCCCTGG AAAAAGTCCT GGAGGCCCTG CGTCCGCACG CGGCCGCGCG
CCTGCTGTGC CTGTTCGGCT GCGGTGGCGA TCGCGATGCC GGCAAGCGTC
CGCTGATGGC TGCGATCGCC GAACGCCTGG CGGATGAGGT GCTGGTCACC
GACGACAACC CGCGCACCGA GGCCAGTGCG GCGATCATCG CCGATATCCG
CAAAGGCTTC GCTGCCGCTG ACAAGGTTAC CTTCCTGCCG TCGCGCGGTG
AGGCGATCGC CCATCTGATC GCTTCCGCTG CGGTGGATGA CGTGGTGCTC
CTGGCCGGCA AGGGTCACGA GGATTATCAG GAGATCGACG GCGTACGCCA
TCCGTTCTCC GACATCGAGC AGGCCGAGCG CGCCCTGGCC GCCTGGGAGG
TGCCGCATGC TTGAGCCTCT TCGCCTCAGC CAGTTGACGG TCGCGCTGG
```

The translation initiation and termination codons are underlined.

The isolated nucleic acid molecule of the present invention can include a ribonucleic or deoxyribonucleic acid molecule, which can be single (coding or noncoding strand) or double stranded, as well as synthetic nucleic acid, such as a synthesized, single stranded polynucleotide.

The present invention also relates to recombinant vectors and recombinant hosts, both prokaryotic and eukaryotic, which contain the substantially purified nucleic acid molecules disclosed throughout this specification.

As used herein a "polynucleotide" is a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region(s) and/or other polynucleotide units commonly used in the art.

An "expression vector" is a polynucleotide having regulatory regions operably linked to a coding region such that, when in a host cell, the regulatory regions can direct the expression of the coding sequence. The use of expression vectors is well known in the art. Expression vectors can be used in a variety of host cells and, therefore, the regulatory regions are preferably chosen as appropriate for the particular host cell.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

Polynucleotides of this invention contain full length or partial length sequences of the MurE gene sequences disclosed herein. Polynucleotides of this invention can be single or double stranded. If single stranded, the polynucleotides can be a coding, "sense," strand or a complementary, "antisense," strand. Antisense strands can be useful as modulators of the gene by interacting with RNA encoding the MurE protein. Antisense strands are preferably less than full length strands having sequences unique or specific for RNA encoding the protein.

The polynucleotides can include deoxyribonucleotides, ribonucleotides or mixtures of both. The polynucleotides can be produced by cells, in cell-free biochemical reactions or through chemical synthesis. Non-natural or modified nucleotides, including inosine, methyl-cytosine, deazaguanosine, etc., can be present. Natural phosphodiester internucleotide linkages can be appropriate. However, polynucleotides can have non-natural linkages between the nucleolides. Non-natural linkages are well known in the art and include, without limitation, methylphosphonates, phosphorothioates, phosphorodithionates, phosphoroamidites and phosphate ester linkages. Dephospho-linkages are also known, as bridges between nucleotides. Examples of these include siloxane, carbonate, carboxymethyl ester, acetamidate, carbamate, and thioether bridges. "Plastic DNA," having, for example, N-vinyl, methacryloxyethyl, methacrylamide or ethyleneimine internucleotide linkages, can be used. "Peptide Nucleic Acid" (PNA) is also useful and resists degradation by nucleases. These linkages can be mixed in a polynucleotide.

As used herein, "purified" and "isolated" are utilized interchangeably to stand for the proposition that the polynucleotide, protein and polypeptide, or respective fragments thereof in question have been removed from the in vivo environment so that they exist in a form or purity not found in nature. Purified or isolated nucleic acid molecules can be manipulated by the skilled artisan, such as but not limited to sequencing, restriction digestion, site-directed mutagenesis, and subcloning into expression vectors for a nucleic acid fragment as well as obtaining the wholly or partially purified protein or protein fragment so as to afford the opportunity to generate polyclonal antibodies, monoclonal antibodies, or perform amino acid sequencing or peptide digestion. Therefore, the nucleic acids claimed herein can be present in whole cells or in cell lysates or in a partially or substantially purified form. It is preferred that the molecule be present at a concentration at least about five-fold to ten-fold higher than that found in nature. A polynucleotide is considered substantially pure if it is obtained purified from cellular components by standard methods at a concentration of at least about 100-fold higher than that found in nature. A polynucleotide is considered essentially pure if it is obtained at a concentration of at least about 1000-fold higher than that found in nature. We most prefer polynucleotides that have been purified to homogeneity, that is, at least 10,000–100,000 fold. A chemically synthesized nucleic acid sequence is considered to be substantially purified when purified from its chemical precursors by the standards stated above.

Included in the present invention are assays that employ further novel polynucleotides that hybridize to $P.$ $aeruginosa$ murE sequences under stringent conditions. By way of example, and not limitation, a procedure using conditions of high stringency is as follows: Prehybridization of filters containing DNA is carried out for 2 hr. to overnight at 65° C. in buffer composed of 6×SSC, 5× Denhardt's solution, and 100 µg/ml denatured salmon sperm DNA. Filters are hybridized for 12 to 48 hrs at 65° C. in prehybridization mixture containing 100 µg/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography.

Other procedures using conditions of high stringency would include either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook, et al., 1989, Molecular Cloning: A Laboratory Manual, second edition, Cold Spring Harbor laboratory Press. In addition to the foregoing, other conditions of high stringency which may be used are well known in the art.

Polypeptides

A preferred aspect of the present invention is a substantially purified form of the MurE protein from *Pseudomonas aeruginosa*. A preferred embodiment is a protein that has the amino acid sequence which is shown in FIG. 1, in SEQ ID NO:2 and disclosed as follows:
MetProMetSerLeuSerGlnLeuPheProGlnAlaGluArgAspLeu-
LeuIleArgGluLeuThrLeuAspSerHisGlyValArgProValAsp-
LeuPheLeuThrValProGlyGlyHisGlnAspGlyArgAlaHisIle-
AlaAspAlaLeuThrLysGlyAlaThrAlaValAlaTyrGluAlaGlu-
GlyAlaGlyGluLeuProProSerAspAlaProLeuIleAlaValLys-
GlyLeuAlaAlaGlnLeuSerAlaValAlaGlyArgPheTyrGlyClu-
ProSerArgGlyLeuAspLeuIleGlyValThrGlyThrAsnGlyLys- ThrSerValSerGlnLeuValAlaGlnAlaLeuAspLeuLeuGlyGlu-
ArgCysGlyIleValGlyThrLeuGlyThrGlyPheTyrGlyAlaLeu-
GluSerGlyArgHisThrThrProAspProLeuAlaValGlnAlaThr-
LeuAlaThrLeuLysGlnAlaGlyAlaArgAlaValAlaMetGluVal-
SerSerHisGlyLeuAspGlnGlyArgValAlaAlaLeuGlyPheAsp-
IleAlaValPheThrAsnLeuSerArgAspHisLeuAspTyrHisGly-
SerMetGluAlaTyrAlaAlaAlaLysAlaLysLeuPheAlaTrpPro-
AspLeuArgCysArgValIleAsnLeuAspAspAspPheGlyArg-
ArgLeuAlaGlyGluGluGlnAspSerGluLeuIleThrTyrSerLeu-
ThrAspSerSerAlaPheLeuTyrCysArgGluAlaArgPheGlyAsp-
AlaGlyIleGluAlaAlaLeuValThrProHisGlyGluGlyLeuLeu-
ArgSerProLeuLeuGlyArgPheAsnLeuSerAsnLeuLeuAlaAla-
ValGlyAlaLeuLeuGlyLeuGlyTyrProLeuGlyAspIleLeuArg-
ThrLeuProGlnLeuGlnGlyProValGlyArgMetGlnArgLeu-
GlyGlyGlyGlyLysProLeuValValValAspTyrAlaHisThrPro-
AspAlaLeuGluLysValLeuGluAlaLeuArgProHisAlaAlaAla-
ArgLeuLeuCysLeuPheGlyCysGlyGlyAspArgAspAlaGly-
LysArgProLeuMetAlaAlaIleAlaGluArgLeuAlaAspGlu-
ValLeuValThrAspAspAsnProArgThrGluAlaSerAlaAlaIle-
IleAlaAspIleArgLysGlyPheAlaAlaAlaAspLysValThrPhe-
LeuProSerArgGlyGluAlaIleAlaHisLeuIleAlaSerAlaAla-
ValAspAspValValLeuLeuAlaGlyLysGlyHisGluAspTyrGln-
GluIleAspGlyValArgHisProPheSerAspIleGluGlnAlaGlu-
ArgAlaLeuAlaAlaTrpGluValProHisAla (SEQ ID NO:2)

The present invention also relates to biologically active fragments and mutant or polymorphic forms of MurE polypeptide sequence as set forth as SEQ ID NO: 2, including but not limited to amino acid substitutions, deletions, additions, amino terminal truncations and carboxy-terminal truncations such that these mutations provide for proteins or protein fragments of diagnostic, therapeutic or prophylactic use and would be useful for screening for modulators, and/or inhibitors of MurE function.

Using the disclosure of polynucleotide and polypeptide sequences provided herein to isolate polynucleotides encoding naturally occurring forms of MurE, one of skill in the art can determine whether such naturally occurring forms are mutant or polymorphic forms of MurE by sequence comparison. One can further determine whether the encoded protein, or fragments of any MurE protein, is biologically active by routine testing of the protein or fragment in a in vitro or in vivo assay for the biological activity of the MurE protein. For example, one can express N-terminal or C-terminal truncations, or internal additions or deletions, in host cells and test for their ability to catalyze the ATP-dependent addition of m-Dap to the D-Glutamine residue of the UDP-N-acetylmuramyl-L-alanine-D-Glutamine precursor.

It is known that there is a substantial amount of redundancy in the various codons which code for specific amino acids. Therefore, this invention is also directed to those DNA sequences that encode RNA comprising alternative codons which code for the eventual translation of the identical amino acid. Therefore, the present invention discloses codon redundancy which can result in different DNA molecules encoding an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. However, any given change can be examined for any effect on biological function by simply assaying for the ability to catalyze the ATP-dependent addition of m-Dap to the D-Glutamine residue of the UDP-N-acetylmuramyl-L-alanine-D-Glutamine precursor as compared to an unaltered MurE protein.

It is known that DNA sequences coding for a peptide can be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate.

As used herein, a "biologically active equivalent" or "functional derivative" of a wild-type MurE possesses a biological activity that is substantially similar to the biological activity of a wild type MurE. The term "functional derivative" is intended to include the "fragments," "mutants," "variants," "degenerate variants," "analogs," "orthologues," and "homologues" and "chemical derivatives" of a wild type MurE protein that can catalyze the ATP-dependent addition of m-Dap to the D-Glutamine residue of of the UDP-N-acetylmuramyl-L-alanine-D-Glutamine precursor.

The term "fragment" refers to any polypeptide subset of wild-type MurE. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the MurE or MurE functional derivative. The term "variant" refers to a molecule substantially similar in structure and function to either the entire wild-type protein or to a fragment thereof. A molecule is "substantially similar" to a wild-type MurE-like protein if both molecules have substantially similar structures or if both molecules possess similar biological activity. Therefore, if the two molecules possess substantially similar activity, they are considered to be variants even if the exact structure of one of the molecules is not found in the other or even if the two amino acid sequences are not identical. The term "analog" refers to a molecule substantially similar in function to either the full-length MurE protein or to a biologically active fragment thereof.

As used herein in reference to a MurE gene or encoded protein, a "polymorphic" MurE is a MurE that is naturally found in the population of *Pseudomonads* at large. A polymorphic form of MurE can be encoded by a different nucleotide sequence from the particular murE gene disclosed herein as SEQ ID NO: 1. However, because of silent mutations, a polymorphic murE gene can encode the same or different amino acid sequence as that disclosed herein. Further, some polymorphic forms MurE will exhibit biological characteristics that distinguish the form from wild-type MurE activity, in which case the polymorphic form is also a mutant.

A protein or fragment thereof is considered purified or isolated when it is obtained at least partially free from it's natural environment in a composition or purity not found in nature. It is preferred that the molecule be present at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature. We most prefer proteins that have been purified to homogeneity, that is, at least 10,000–100,000 fold.

Probes and Primers

Polynucleotide probes comprising full length or partial sequences of SEQ ID NO: 1 can be used to determine whether a cell or sample contains *P. aeruginosa* MurE DNA or RNA. The effect of modulators that effect the transcription of the murE gene can be studied via the use of these probes. A preferred probe is a single stranded antisense probe having at least the full length of the coding sequence of MurE. It is also preferred to use probes that have less than the full length sequence, and contain sequences specific for *P. aeruginosa* murE DNA or RNA. The identification of a sequence(s) for use as a specific probe is well known in the art and involves choosing a sequence(s) that is unique to the target sequence, or is specific thereto. It is preferred that polynucleotides that are probes have at least about 25 nucleotides, more preferably about 30 to 35 nucleotides. The longer probes are believed to be more specific for *P. aeruginosa* murE gene(s) and RNAs and can be used under more stringent hybridization conditions. Longer probes can be used but can be more difficult to prepare synthetically, or can result in lower yields from a synthesis. Examples of sequences that are useful as probes or primers for *P. aeruginosa* murEgene(s) are Primer A (sense) 5-TTT CATATGCCTATGAGCCTGAGCCAAC-3' (SEQ ID NO:3) and Primer B (antisense) 5'-TTT GGATCCTCAAGCATGCGGCACCTC-3' (SEQ ID NO:4). These primers are nucleotides 1–22 (A) and the complement of nucleotides 1447–1464 (B) respectively, of SEQ ID NO: 1. Restriction sites, underlined, for NdeI and BamHI are added to the 5' ends of the primers to allow cloning between the NdeI and BamHI sites of the expression vector pET-15b. However, one skilled in the art will recognize that these are only a few of the useful probe or primer sequences that can be derived from SEQ ID NO:1.

Polynucleotides having sequences that are unique or specific for *P. aeruginosa* murE can be used as primers in amplification reaction assays. These assays can be used in tissue typing as described herein. Additionally, amplification reactions employing primers derived from *P. aeruginosa* murE sequences can be used to obtain amplified *P. aeruginosa* murE DNA using the murE DNA of the cells as an initial template. The murE DNA so obtained can be a mutant or polymorphic form of *P. aeruginosa* murE that differs from SEQ ID NO: 1 by one or more nucleotides of the MurE open reading frame or sequences flanking the ORF. The differences can be associated with a non-defective naturally occurring form or with a defective form of MurE. Thus, polynucleotides of this invention can be used in identification of various polymorphic *P. aeruginosa* murE genes or the detection of an organism having a *P. aeruginosa* murE gene. Many types of amplification reactions are known in the art and include, without limitation, Polymerase Chain Reaction, Reverse Transcriptase Polymerase Chain Reaction, Strand Displacement Amplification and Self-Sustained Sequence Reaction. Any of these or like reactions can be used with primers derived from SEQ ID NO: 1.

Expression of MurE

A variety of expression vectors can be used to express recombinant MurE in host cells. Expression vectors are defined herein as nucleic acid sequences that include regulatory sequences for the transcription of cloned DNA and the translation of their mRNAs in an appropriate host. Such vectors can be used to express a bacterial gene in a variety of hosts such as bacteria, bluegreen algae, plant cells, insect cells and animal cells. Specifically designed vectors allow the shuttling of genes between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and regulatory sequences. A promoter is defined as a regulatory sequence that directs RNA polymerase to bind to DNA and initiate RNA synthesis. A strong promoter is one which causes mRNAs to be initiated at high frequency. Expression vectors can include, but are not limited to, cloning vectors, modified cloning vectors, specifically designed plasmids or viruses.

In particular, a variety of bacterial expression vectors can be used to express recombinant MurE in bacterial cells. Commercially available bacterial expression vectors which are suitable for recombinant MurE expression include, but are not limited to pQE (QIAGEN), pET11a or pET15 (NOVAGEN), lambda gt11 (INVITROGEN), and pKK223-3 (PHARMACIA).

Alternatively, one can express murE DNA in cell-free transcription-translation systems, or murE RNA in cell-free translation systems. Cell-free synthesis of MurE can be in batch or continuous formats known in the art.

One can also synthesize MurE chemically, although this method is not preferred.

A variety of host cells can be employed with expression vectors to synthesize MurE protein. These can include *E. coli*, *Bacillus*, and *Salmonella*. Insect and yeast cells can also be appropriate.

Following expression of MurE in a host cell, MurE polypeptides can be recovered. Several protein purification procedures are available and suitable for use. MurE protein and polypeptides can be purified from cell lysates and extracts, or from culture medium, by various combinations of, or individual application of methods including ultrafiltration, acid extraction, alcohol precipitation, salt fractionation, ionic exchange chromatography, phosphocellulose chromatography, lecithin chromatography, affinity (e.g., antibody or His-Ni) chromatography, size exclusion chromatography, hydroxylapatite adsorption chromatography and chromatography based on hydrophobic or hydrophillic interactions. In some instances, protein denaturation and refolding steps can be employed. High performance liquid chromatography (HPLC) and reversed phase HPLC can also be useful. Dialysis can be used to adjust the final buffer composition.

The MurE protein itself is useful in assays to identify compounds that modulate the activity of the protein—including compounds that inhibit the activity of the protein. The MurE protein is also useful for the generation of antibodies against the protein, structural studies of the protein, and structure/function relationships of the protein.

Modulators and Inhibitors of MurE

The present invention is also directed to methods for screening for compounds which modulate or inhibit a MurE protein. Compounds which modulate or inhibit MurE can be DNA, RNA, peptides, proteins, or non-proteinaceous organic or inorganic compounds or other types of molecules. Compounds that modulate the expression of DNA or RNA encoding MurE or are inhibitors of the biological function of MurE can be detected by a variety of assays. The assay can be a simple "yes/no" assay to determine whether there is a change in expression or function. The assay can be made quantitative by comparing the expression or function of a test sample with the levels of expression or function in a standard sample, that is, a control. A compound that is a modulator can be detected by measuring the amount of the MurE produced in the presence of the compound. An compound that is an inhibitor can be detected by measuring the specific activity of the MurE protein in the presence and absence of the compound.

The proteins, DNA molecules, RNA molecules and antibodies lend themselves to the formulation of kits suitable for the detection and anaysis of MurE. Such a kit would comprise a compartmentalized carrier suitable to hold in close confinement at least one container. The carrier would further comprise reagents such as recombinant MurE or anti-MurE antibodies suitable for detecting MurE. The carrier can also contain a means for detection such as labeled antigen or enzyme substrates or the like.

Pharmaceutical Compositions

Pharmaceutically useful compositions comprising a modulator or inhibitor of MurE can be formulated according to known methods such as by the admixture of a pharmaceutically acceptable carrier. Examples of such carriers and methods of formulation can be found in Remington's Pharmaceutical Sciences. To form a pharmaceutically acceptable composition suitable for effective administration, such compositions will contain an effective amount of the inhibitor.

Therapeutic, prophylactic or diagnostic compositions of the invention are administered to an individual in amounts sufficient to treat, prevent or diagnose disorders. The effective amount can vary according to a variety of factors such as the individual's condition, weight, sex and age. Other factors include the mode of administration. The appropriate amount can be determined by a skilled physician The pharmaceutical compositions can be provided to the individual by a variety of routes such as subcutaneous, topical, oral and intramuscular.

The term "chemical derivative" describes a molecule that contains additional chemical moieties which are not normally a part of the base molecule. Such moieties can improve the solubility, half-life, absorption, etc. of the base molecule. Alternatively the moieties can attenuate undesirable side effects of the base molecule or decrease the toxicity of the base molecule. Examples of such moieties are described in a variety of texts, such as Remington's Pharmaceutical Sciences.

Compounds identified according to the methods disclosed herein can be used alone at appropriate dosages. Alternatively, co-administration or sequential administration of other agents can be desirable.

The present invention also provides a means to obtain suitable topical, oral, systemic and parenteral pharmaceutical formulations for use in the methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention can be administered in a single daily dose, or the total daily dosage can be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are presented by the way of illustration and, because various other embodiments will be apparent to those in the art, the following is not to be construed as a limitation on the scope of the invention. For example, while particular preferred embodiments of the invention are presented herein, it is within the ability of persons of ordinary skill in the art to modify or substitute vectors, host cells, compositions, etc., or to modify or design protocols or assays, all of which may reach the same or equivalent performance or results as the embodiments shown herein.

EXAMPLE 1

General Materials and Methods

All reagents were purchased from SIGMA CHEMICAL CO., St. Louis, Mo., unless otherwise indicated. UDP-N-acetylmuramyl-L-alanine was synthesized and purified by a method known in the art (Jin, H., Emanuele, J. J., Jr., Fairman, R., Robertson, J. G., Hail, M. E., Ho, H.-T., Falk, P. and Villafranca, J. J, 1996. Structural studies of *Escherichia coli* UDP-N-acetylmuramate: L-alanine ligase, Biochemistry 35: 14423–14431).

DNA manipulations reagents and techniques. Restriction endonucleases and T4 ligase were obtained from GIBCO-BRL. Agarose gel electrophoresis and plasmid DNA preparations were performed according to published procedures (Sambrook, J., E. F. Fritsch, and T. Maniatis, 1989, Molecular cloning: a L, Laboratory Manual, 2nd ed. Cold Spring Harbor, N.Y.: Cold Spring Harbor Laboratory). Recombinant plasmids containing *P. aeruginosa* murE were propagated in *E. coli* DH5a (GIBCO-BRL, Rockville, Md.) prior to protein expression in *E. coli* BL21(DE3)/plysS (NOVAGEN, Madison, Wis.). SDS-PAGE was performed with precast gels (NOVAGEN). DNA sequences were determined using an automated ABI PRISM™ DNA sequencer (PERKIN-ELMER ABI, Foster City, Calif.).

EXAMPLE 2

Cloning of *Pseudomonas aeruginosa* murE

Genomic DNA from *P. aeruginosa* (strain MB4439) was prepared from 100 ml late stationary phase culture in Brain Heart Infusion broth (DIFCO, Detroit, Mich.). Cells were washed with 0.2 M sodium acetate, suspended in 10 ml of TEG (100 mM Tris, pH 7, containing 10 mM EDTA and 25% glucose) and lysed by incubation with 200 µg of N-acetylmuramidase (Sigma) for 1 h at 37° C. Chromosomal DNA was purified from the cell lysate using a QIAGEN (Santa Clarita, Calif.) genomic DNA preparation kit and following the manufacturers protocol. Briefly, the cell lysate was treated with protease K at 50° C. for 45 min, loaded onto an equilibrated QIAGEN genomic tip, entered into the resin by centrifugation at 3000 rpm for 2 min. Following washing the genomic tip, the genomic DNA was eluted in distilled water and kept at 4° C. Approximately 50 ng genomic DNA was used as a template in PCR reactions to clone murE.

Two oligonucleotide primers (GIBCO/BRL, Bethesda, Md.) complementary to sequences at the 5' and the 3' ends of *P. aeruginosa* murE were used to clone this gene using KLENTAQ ADVANTAGE™ polymerase (CLONTECH, Palo Alto, Calif.). The primer nucleotide sequences were as follows: 5'-TTTCATATGCCTATGAGCCTGAGCCAAC-3' (SEQ ID NO:3) (a NdeI linker plus nucleotides 1–22 of SEQ ID NO: 1) and 5'-TTT GGATCCTCAAGCATGCGGCACCTC-3' (SEQ ID NO:4) (a BamH1 linker plus the complement of nucleotides 1447–1464 of SEQ ID NO: 1). A PCR product representing *P. aeruginosa* murE was verified by nucleotide sequence, digested with NdeI and BamHI, and cloned between the NdeI and BamHI sites of pET-15b, creating plasmid pPae-MurE. This plasmid was used for expression of the murE gene in *E. coli*.

EXAMPLE 3

Sequence Analysis of *Pseudomonas aeruginosa* murE

The nucleotide sequence of murE, determined in both orientations, and the deduced amino acid sequence of the MurE protein is depicted in FIG. 1. Sequence comparison using the BLAST (Altschul, S. F., Gish, W., Miller, W., Myers, E. W. & Lipman, D. J. (1990) "Basic local alignment search tool." J. Mol. Biol. 215:403–410) algorithm against the GenBank database showed that, to varying degrees, the cloned region is homologous (65% similar, 48% identical) to murE gene from *E. coli* (Tao, J. S, and E. E., Ishiguro, 1989. Nucleotide sequence of the murE gene of *Escherichia coli*. Can. J. Microbiol. 35:1051–1054).

EXAMPLE 4

Overexpression, Purification and Enzymatic Activity of *Pseudomonas aeruginosa* MurE murE was cloned into the expression vector pET-15b (NOVAGEN) as described above to create plasmid pPae-MurE. The pET-15b vector incorporates the 6×Histidine-tag into the protein construct to allow rapid purification of MurE by affinity chromatography. The pET (Plasmids for Expression by T7 RNA polymerase) plasmids are derived from pBR322 and designed for protein over-production in *E. coli*. The vector pET-15b contains the ampicillin resistance gene, ColE1 origin of replication in addition to T7 phage promoter and terminator. The T7 promoter is recognized by the phage T7 RNA polymerase but not by the *E. coli* RNA polymerase. A host *E. coli* strain such as BL21(DE3)pLysS is engineered to contain integrated copies of T7 RNA polymerase under the control of lacUV5 that is inducible by IPTG. Production of a recombinant protein in the *E. coli* strain BL21(DE3) pLysS occurs after expression of T7RNA polymerase is induced.

The pPaeMurE plasmid was introduced into the host strain BL21 DE3/pLysS (NOVAGEN) for expression of His-tagged MurE. Colonies were grown at 37° C. in 100 ml of LB broth containing 100 mg/ml ampicillin and 32 μg/ml chloramphenicol. When cultures reached a cell density of $A_{600}$=0.5, cells were pelleted and then resuspended in M9ZB medium (NOVAGEN) containing 1 mM IPTG. Cells were induced for 3 h at 30° C., pelleted at 3000 g, and frozen at −80° C.

Cultures containing either the recombinant plasmid pPae-MurE or the control plasmid vector, pET-15b were grown at 30° C. and induced with IPTG. Cells transformed with pPaeMurE contained an inducible protein of approximately 54.7 kDa, corresponding to the expected size of *P. aeruginosa* MurE protein as shown by SDS-PAGE. There were no comparable detectable protein bands after induction of cells transformed with the control plasmid vector, pET-15b.

Purification of Recombinant MurE Enzyme.

The cell pellet from 100 ml of induced culture prepared as described above was resuspended in 10 ml BT buffer (50 mM bis-tris-propane, pH 8.0, containing 100 mM potassium chloride and 1% glycerol) at 4° C. Cells were lysed either by freeze-thaw or by French Press. After centrifugation, the supernatant was mixed with 15 ml of freshly prepared TALON (CLONTECH) resin and incubated for 30 min at room temp. The resin was washed twice by centrifugation with 25 ml of BT buffer at room temperature. Finally, the resin was loaded into a column and washed with 20 ml of BT, pH 7.0, containing 5 mM imidazole. Protein was eluted with 20 ml of BT buffer pH 8.0, containing 100 mM imidazole. Fractions (0.5 ml) were collected and analyzed by SDS-Gel electrophoresis.

Figure 2:
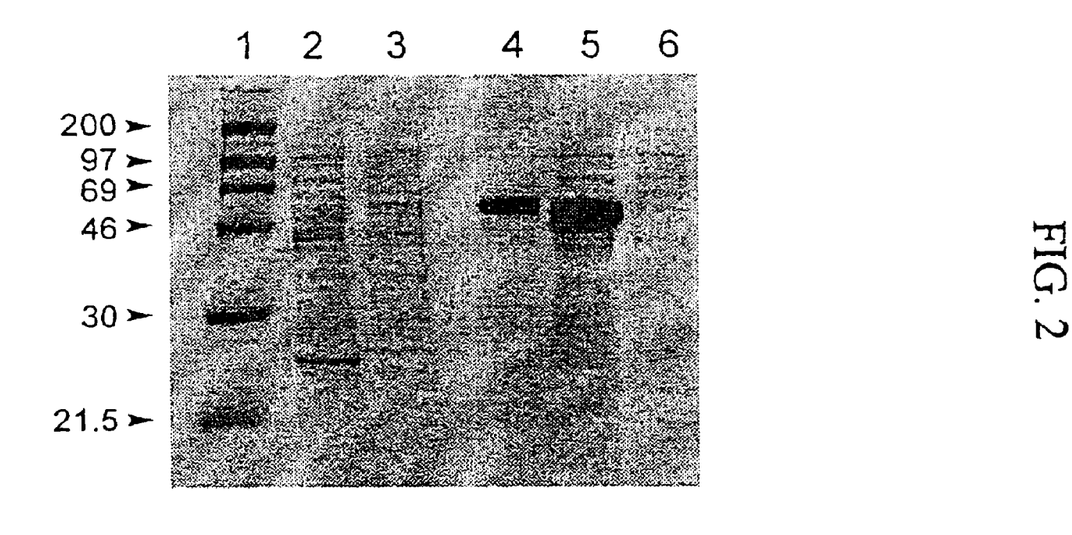
FIG. 2. Production of recombinant *P. aeruginosa* MurE. Aliquots from cell lysates, either uninduced or induced with IPTG, and column-purified polypeptides were analyzed by SDS-PAGE. Lane 1, Molecular weight markers; Lane2, IPTG-induced lysate of cells (BL21(DE3)/pLysS) containing the control vector pET-15b; Lane 3, uninduced cell lysate containing the control vector pET-15b; lane 4, column-purified MurE; Lane 5 IPTG-induced lysate of cells expressing MurE; Lane 6, uninduced lysate of cells containing murE.

Aliquots from cell lysates, either uninduced or induced with IPTG, and column-purified polypeptides were analyzed by SDS-PAGE. (FIG. 2) Lane 1, Molecular weight markers; Lane2, IPTG-induced lysate of cells (BL21(DE3)/pLysS) containing the control vector pET-15b; Lane 3, uninduced cell lysate containing the control vector pET-15b; lane 4, column-purified MurE; Lane 5 IPTG-induced lysate of cells expressing MurE; Lane 6, uninduced lysate of cells containing murE.

This resulted in a partially purified preparation of *P. aeruginosa* MurE protein that could be used in activity assays. The protein may be purified further, if desired, using methods known in the art.

Assay for Activity of MurE Enzyme

The ATP-dependent MurE activity was assayed by monitoring the formation of product ADP using the pyruvate kinase and lactate dehydrogenase coupled enzyme assay. The reaction was monitored spectrophotometrically.

Typically, the assay contained 100 mM BIS-TRIS-propane, pH 8.0, 200 μM NADH, 1 mM ATP, 20 mM PEP, 5 mM $MgCl_2$, 1 mM DTT, 350 μM UDP-N-acetyl-muramyl-L-alanine-D-Glutamine, 1 mM m-Dap, 33 units/ml of pyruvate kinase and 1660 units/ml of lactate dehydrogenase in a final volume of 200 or 400 μl. The mixture was incubated at 25° C. for 5 min and the reaction initiated by the addition of 1–10 μg of MurE. These conditions are one example of an assay useful for evaluating the activity of MurE. Other assays can be used, or amounts of buffers, substrate and enzyme can be changed, as desired, to alter the rate of production of ADP.

ADP formation was monitored by the decrease in absorbance at 340 nm as a function of time using a MOLECULAR DEVICES SPECTRAMAXPLUS™ microtiterplate spectrophotomer (for 200 μl assays) or a HEWLETT-PACKARD HP8452A spectrophotometer equipped with a circulating water bath (for 400 μl assays). Rates were calculated from the linear portions of the progress curves using the extinction coefficient for NADH, e=6220 $cm^{-1}$ M-1. One unit of MurE activity is equal to 1 μmol of ADP formed per min at 25° C.

TABLE 1

Specific activities of recombinant MurE
from *E. coli* and *P. aeruginosa*

| Mur Ligase | P. aeruginosa<br>μmol × min$^{-1}$ × mg$^{-1}$ | E. coli<br>μmol × min$^{-1}$ × mg$^{-1}$ |
|---|---|---|
| MurE | 3.31 | 0.68 |

EXAMPLE 5
Screening for Inhibitors of MurE

One assay for the measurement of the activity of MurE is provided in Example 4. That assay, and other assays for MurE activity can be adapted for screening assays to detect inhibitors of MurE. For example, for inhibition assays, inhibitors in DMSO are added at the desired concentration to the assay mixture. In a separate, control reaction, only DMSO is added to the assay mixture. The reactions are initiated by the addition of enzyme (MurE). Rates are calculated as described above. Relative activities are calculated from the equation 1:

$$\text{relative activity} = \text{rate with inhibitor/rate without inhibitor.} \quad (1)$$

Inhibition constant ($IC_{50}$) values are determined from a range of inhibitor concentrations and calculated from equation 2.

$$\text{relative activity} = 1/(1 + [I]/IC_{50}) \quad (2)$$

One can use computer software to assist in the analysis, e.g., SIGMA PLOT™ (JANDEL SCIENTIFIC, San Rafeal, Calif.).

We prefer inhibitors of MurE that result in relative activities of the MurE enzyme of at least less than 75%, more preferably, 25–50% or 10–25%. We most prefer inhibitors resulting in relative activities of less than 20%, particularly less than 10% of the activity of MurE in the absence of the inhibitor.

We also prefer inhibitors that effectively lower the relative activity of MurE when the inhibitor is present at a very low concentration.

EXAMPLE 6
Therapy Using Inhibitors of MurE

A patient presenting with an indication of infection with a microorganism susceptible to inhibitors of MurE, e.g., gram positive and negative bacteria, including *P. aeruginosa*, can be treated by administration of inhibitors of MurE. Physicians skilled in the art are familiar with administering therapeutically effective amounts of inhibitors or modulators of microbial enzymes. Such skilled persons can readily determine an appropriate dosing scheme to achieve a desired therapeutic effect.

Therapy can also be prophylactic. For example, a patient at risk for developing a bacterial infection, including infection with *P. aeruginosa*, can be treated by administration of inhibitors of MurE. Physicians skilled in the art are familiar with administering therapeutically effective amounts of inhibitors or modulators of microbial enzymes. Such skilled persons can readily determine an appropriate dosing scheme to achieve a desired therapeutic effect.

What is claimed is:

1. An isolated and purified polynucleotide selected from the group consisting of:
   (a) a polynucleotide encoding a polypeptide having the amino acid sequence of SEQ ID NO: 2, and
   (b) a polynucleotide which is fully complementary to the polynucleotide of (a).

2. The polynucleotide of claim 1 comprising the nucleotide sequence of SEQ ID NO: 1.

3. An expression vector comprising the polynucleotide of claim 1.

4. An isolated host cell comprising the expression vector of claim 3.

* * * * *

SEQUENCE LISTING

<160> NUMBER OF SEQ ID NOS: 4

<210> SEQ ID NO 1
<211> LENGTH: 1499
<212> TYPE: DNA
<213> ORGANISM: Pseudomonas aeruginosa

<400> SEQUENCE: 1

```
atgcctatga gcctgagcca actgtttccc caggccgagc gcgatctgct gatccgcgag      60
ctgaccctgg atagccacgg cgttcgtccg gtcgacctgt tcctgacggt tccgggcggg     120
caccaggatg gtcgtgcgca catcgccgat gccctgacca agggcgcgac tgccgtggct     180
tacgaggcgg aaggcgccgg agagttgccg cccagcgatg cgccgctgat cgcggtgaag     240
gggctggccg cgcaactgtc ggcggtcgcc gggcgtttct acggcgagcc gagccgcggg     300
ctggacctga tcggcgtcac cggcaccaac ggcaagacca gcgtcagcca actggtggcc     360
caggccctgg atctgctcgg cgagcgctgc ggcatcgtcg gcaccctcgg caccggtttc     420
tacgcgcgcc tggagagcgg ccggcacacc acgccggacc cgctcgcggt gcaggccacg     480
ctggccacgc tgaagcaggc cggcgcccgc gcggtagcga tggaagtgtc ttcccacggc     540
ctcgaccagg gccgcgtggc ggcgctcggc ttcgatatcg cggtgttcac caatctgtcc     600
cgcgaccacc tcgactatca cggttcgatg gaagcctatg ccgccgccaa ggccaagctg     660
ttcgcctggc cggacctgcg ctgccgggtg atcaacctgg acgacgattt cggccgtcga     720
ctggccggcg aggagcagga ctcggagctg atcacctaca gcctcaccga cagctcggcg     780
ttcctctatt gccgcgaagc gcgcttcggc gacgccggca tcgaggcggc gctggtcact     840
```

-continued

```
ccgcacggcg agggcctgct gcgcagcccg ttgctcggcc gcttcaacct gagcaacctg    900
ctggcggcgg tcggtgcgtt gcttggcctg ggttatcccc tgggcgatat cctccgcact    960
ttgccgcaac tgcaggggcc ggtcggccgc atgcagcgcc tgggaggcgg cggcaagccg   1020
ctggtggtgg tggactacgc gcatactccc gacgccctgg aaaaagtcct ggaggccctg   1080
cgtccgcacg cggccgcgcg cctgctgtgc ctgttcggct gcggtggcga tcgcgatgcc   1140
ggcaagcgtc cgctgatggc tgcgatcgcc gaacgcctgg cggatgaggt gctggtcacc   1200
gacgacaacc cgcgcaccga ggccagtgcg gcgatcatcg ccgatatccg caaaggcttc   1260
gctgccgctg acaaggttac cttcctgccg tcgcgcggtg aggcgatcgc ccatctgatc   1320
gcttccgctg cggtggatga cgtggtgctc ctggccggca agggtcacga ggattatcag   1380
gagatcgacg gcgtacgcca tccgttctcc gacatcgagc aggccgagcg cgccctggcc   1440
gcctgggagg tgccgcatgc ttgagcctct tcgcctcagc cagttgacgg tcgcgctgg    1499
```

<210> SEQ ID NO 2
<211> LENGTH: 487
<212> TYPE: PRT
<213> ORGANISM: Pseudomonas aeruginosa

<400> SEQUENCE: 2

```
Met Pro Met Ser Leu Ser Gln Leu Phe Pro Gln Ala Glu Arg Asp Leu
1               5                   10                  15

Leu Ile Arg Glu Leu Thr Leu Asp Ser His Gly Val Arg Pro Val Asp
                20                  25                  30

Leu Phe Leu Thr Val Pro Gly Gly His Gln Asp Gly Arg Ala His Ile
            35                  40                  45

Ala Asp Ala Leu Thr Lys Gly Ala Thr Ala Val Ala Tyr Glu Ala Glu
        50                  55                  60

Gly Ala Gly Glu Leu Pro Pro Ser Asp Ala Pro Leu Ile Ala Val Lys
65                  70                  75                  80

Gly Leu Ala Ala Gln Leu Ser Ala Val Ala Gly Arg Phe Tyr Gly Glu
                85                  90                  95

Pro Ser Arg Gly Leu Asp Leu Ile Gly Val Thr Gly Thr Asn Gly Lys
            100                 105                 110

Thr Ser Val Ser Gln Leu Val Ala Gln Ala Leu Asp Leu Leu Gly Glu
        115                 120                 125

Arg Cys Gly Ile Val Gly Thr Leu Gly Thr Gly Phe Tyr Gly Ala Leu
    130                 135                 140

Glu Ser Gly Arg His Thr Thr Pro Asp Pro Leu Ala Val Gln Ala Thr
145                 150                 155                 160

Leu Ala Thr Leu Lys Gln Ala Gly Ala Arg Ala Val Ala Met Glu Val
                165                 170                 175

Ser Ser His Gly Leu Asp Gln Gly Arg Val Ala Ala Leu Gly Phe Asp
            180                 185                 190

Ile Ala Val Phe Thr Asn Leu Ser Arg Asp His Leu Asp Tyr His Gly
        195                 200                 205

Ser Met Glu Ala Tyr Ala Ala Lys Ala Lys Leu Phe Ala Trp Pro
    210                 215                 220

Asp Leu Arg Cys Arg Val Ile Asn Leu Asp Asp Phe Gly Arg Arg
225                 230                 235                 240

Leu Ala Gly Glu Glu Gln Asp Ser Glu Leu Ile Thr Tyr Ser Leu Thr
                245                 250                 255
```

-continued

```
Asp Ser Ser Ala Phe Leu Tyr Cys Arg Glu Ala Arg Phe Gly Asp Ala
        260                 265                 270

Gly Ile Glu Ala Ala Leu Val Thr Pro His Gly Glu Gly Leu Leu Arg
        275                 280                 285

Ser Pro Leu Leu Gly Arg Phe Asn Leu Ser Asn Leu Leu Ala Ala Val
        290                 295                 300

Gly Ala Leu Leu Gly Leu Gly Tyr Pro Leu Gly Asp Ile Leu Arg Thr
305                 310                 315                 320

Leu Pro Gln Leu Gln Gly Pro Val Gly Arg Met Gln Arg Leu Gly Gly
                325                 330                 335

Gly Gly Lys Pro Leu Val Val Val Asp Tyr Ala His Thr Pro Asp Ala
        340                 345                 350

Leu Glu Lys Val Leu Glu Ala Leu Arg Pro His Ala Ala Ala Arg Leu
        355                 360                 365

Leu Cys Leu Phe Gly Cys Gly Gly Asp Arg Asp Ala Gly Lys Arg Pro
370                 375                 380

Leu Met Ala Ala Ile Ala Glu Arg Leu Ala Asp Glu Val Leu Val Thr
385                 390                 395                 400

Asp Asp Asn Pro Arg Thr Glu Ala Ser Ala Ala Ile Ile Ala Asp Ile
                405                 410                 415

Arg Lys Gly Phe Ala Ala Ala Asp Lys Val Thr Phe Leu Pro Ser Arg
                420                 425                 430

Gly Glu Ala Ile Ala His Leu Ile Ala Ser Ala Ala Val Asp Asp Val
                435                 440                 445

Val Leu Leu Ala Gly Lys Gly His Glu Asp Tyr Gln Glu Ile Asp Gly
        450                 455                 460

Val Arg His Pro Phe Ser Asp Ile Glu Gln Ala Glu Arg Ala Leu Ala
465                 470                 475                 480

Ala Trp Glu Val Pro His Ala
                485
```

<210> SEQ ID NO 3
<211> LENGTH: 28
<212> TYPE: DNA
<213> ORGANISM: Artificial Sequence
<220> FEATURE:
<223> OTHER INFORMATION: PCR Primer

<400> SEQUENCE: 3
tttcatatgc ctatgagcct gagccaac                                    28

<210> SEQ ID NO 4
<211> LENGTH: 27
<212> TYPE: DNA
<213> ORGANISM: Artificial Sequence
<220> FEATURE:
<223> OTHER INFORMATION: PCR Primer

<400> SEQUENCE: 4
tttggatcct caagcatgcg gcacctc                                     27